US012406421B2

(12) United States Patent
Oberlin et al.

(10) Patent No.: US 12,406,421 B2
(45) Date of Patent: Sep. 2, 2025

(54) AVATAR—BASED BEHAVIOR CHANGING SYSTEM AND METHOD

(71) Applicant: THE TRUSTEES OF INDIANA UNIVERSITY, Bloomington, IN (US)

(72) Inventors: Brandon Oberlin, Indianapolis, IN (US); Andrew Nelson, Indianapolis, IN (US)

(73) Assignee: The Trustees of Indiana University, Bloomington, IN (US)

( * ) Notice: Subject to any disclaimer, the term of this patent is extended or adjusted under 35 U.S.C. 154(b) by 58 days.

(21) Appl. No.: 18/030,936

(22) PCT Filed: Apr. 1, 2022

(86) PCT No.: PCT/US2022/023052
§ 371 (c)(1),
(2) Date: Apr. 7, 2023

(87) PCT Pub. No.: WO2022/216541
PCT Pub. Date: Oct. 13, 2022

(65) Prior Publication Data
US 2023/0386115 A1 Nov. 30, 2023

Related U.S. Application Data

(60) Provisional application No. 63/172,814, filed on Apr. 9, 2021.

(51) Int. Cl.
*G06T 13/40* (2011.01)
*A63F 13/213* (2014.01)
*A63F 13/60* (2014.01)

(52) U.S. Cl.
CPC ............ *G06T 13/40* (2013.01); *A63F 13/213* (2014.09); *A63F 13/60* (2014.09); *A63F 2300/5553* (2013.01); *A63F 2300/8082* (2013.01)

(58) Field of Classification Search
CPC ........ G06T 13/40; A63F 13/213; A63F 13/60; A63F 2300/5553; A63F 2300/8082; A61B 5/0077; A61B 5/16; A61B 5/744
See application file for complete search history.

(56) References Cited

U.S. PATENT DOCUMENTS 6,425,764 B1 * 7/2002 Lamson ................. G16H 30/40
434/236
10,832,589 B1   11/2020 Anzalone et al.
(Continued)

FOREIGN PATENT DOCUMENTS

WO    2015192117 A1   12/2015

OTHER PUBLICATIONS

Freeman, Guo, and Divine Maloney. "Body, avatar, and me: The presentation and perception of self in social virtual reality." Proceedings of the ACM on human-computer interaction 4.CSCW3 (2021): 1-27. (Year: 2021).*

(Continued)

*Primary Examiner* — William A Beutel
*Assistant Examiner* — Chris Alejandro Puntier
(74) *Attorney, Agent, or Firm* — Taft Stettinius & Hollister LLP

(57) ABSTRACT

A behavioral change observation system for inducing a behavioral change of a subject generated via virtual reality interactions with avatars comprises an image capturing/streaming device configured to capture a reaction of the subject as the subject is responding to each interactive session and an avatar reaction computing device. The image capturing/streaming device streams to the subject a plurality of interactive sessions each including an avatar and an environment in which each avatar is presented. The avatar reaction computing device captures reaction data from the subject as the subject observes each interactive session, and (Continued)

incorporates the reaction data into a psychological assessment of the subject.

11 Claims, 7 Drawing Sheets

(56) References Cited

U.S. PATENT DOCUMENTS 11,100,695 B1 * 8/2021 O'Hagan ................ G06T 13/40
2017/0206795 A1 7/2017 Kaleal, III

OTHER PUBLICATIONS

Hayeon Song, Jihyun Kim, Remi J. Kwon, Younbo Jung, Anti-smoking educational game using avatars as visualized possible selves, Computers in Human Behavior, vol. 29, Issue 5, (Year: 2013).*

European Patent Office (EPO) Munich, Germany; The extended European Search Report of the corresponding Application No. 22785195.3; Date: Jan. 7, 2025; pp. 1-10; Examiner: Costa Angeli, M.

Senel, Gizem, et al: "Conversation with Your Future Self About Nicotine Dependence", SPRINGER; pp. 216-223, XP047591111.

* cited by examiner

AVATAR—BASED BEHAVIOR CHANGING SYSTEM AND METHOD

CROSS-REFERENCE TO RELATED APPLICATIONS

This application is a U.S. National Phase application of International Application No. PCT/US2022/023052, which was filed on Apr. 1, 2022, and which claims priority to U.S. Provisional Application No. 63/172,814, which was filed on Apr. 9, 2021, the contents of which are hereby incorporated by reference in their entirety.

STATEMENT ON FEDERALLY SPONSORED RESEARCH OR DEVELOPMENT

This invention was made with government support under TR001108 awarded by National Institutes of Health. The Government has certain rights in the invention.

FIELD OF THE DISCLOSURE

The present disclosure relates to behavior changing system and methods, and more particularly, to systems and methods for streaming avatars in virtual realities, where the avatars are based on a subject that is experiencing the virtual realities to observe and change the behavior of the subject.

BACKGROUND

An avatar is a virtual representation of a person or other living being. Avatars have been used to represent people in several applications such as video games. More recently, avatars have been streamed to users in virtual reality experiences. For example, a user's own avatar may be streamed to that user in virtual reality. Avatars can represent a user's appearance in a virtual world, which may influence the user's behavior in the real world.

Studies have shown that addiction disorders are characterized by discounting future costs and benefits. Greater valuation of future costs and benefits predicts lower substance use and abuse and better treatment outcomes.

As described herein, greater valuation of future costs and benefits may be achieved through interaction with avatars in virtual realities via a specific arrangement of process steps. Therefore, what is needed is a system and method for introducing subjects to avatars in virtual realities in which the avatars present aspects of a subject's alternative futures, both verbally and visually by presentation of the avatars' physical appearance.

SUMMARY

In an illustrative embodiment, a behavioral change observation system for inducing a behavioral change of a subject generated via a plurality of virtual reality interactions with a plurality of avatars comprises an image capturing/streaming device. The image capturing/streaming device is configured to capture a reaction of the subject as the subject is responding to each interactive session that is streamed to the subject. The system further includes one or more processors in communication with the image capturing/streaming device and a memory in communication with the one or more processors and storing program code that, when executed by at least one of the one or more processors, causes the system to: stream to the subject utilizing the image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment that each avatar is presented in corresponds to an outcome of the subject based on decisions executed by the subject between a present time and a future time.

In some embodiments, the one or more processors is further configured to cause the system to: capture reaction data from the subject as the subject observes each interactive session streamed to the subject, wherein the reaction data is generated from the subject reacting to each avatar interaction streamed to the subject.

In some embodiments, the one or more processors is further configured to cause the system to: incorporate the reaction data into a psychological assessment of the subject based on how the subject reacted to each avatar interaction streamed to the subject in each interactive session.

In some embodiments, each environment in which each avatar is presented in includes differences in at least one of: (i) material items desired by the subject and (ii) general indicators of affluence.

In another illustrative embodiment, a method for inducing a behavioral change of a subject generated via a plurality of virtual reality interactions with a plurality of avatars comprises streaming to the subject utilizing an image capturing/streaming device a plurality of interactive sessions with each interactive session that is streamed including an interaction with an avatar from a plurality of interactions with avatars and an environment in which each avatar is presented from a plurality of environments in which each avatar is presented in.

In some embodiments, at least one of: (i) a physical appearance of each avatar and (ii) the environment in which each avatar is presented in corresponds to different outcomes of the subject based on decisions executed by the subject between a present time and a future time, wherein the environment in which each avatar is presented is based at least one of material items desired by the subject and general indicators of affluence.

In some embodiments, streaming images to a subject utilizing an image capturing/streaming device further includes capturing reaction data from the subject as the subject observes each interactive session streamed to the subject.

In some embodiments, the reaction data is generated from the subject reacting to each avatar interaction streamed to the subject including each avatar and each corresponding physical appearance of each avatar.

In some embodiments, streaming images to a subject utilizing an image capturing/streaming device further includes incorporating the reaction data into a psychological assessment of the subject based on how the subject reacted to each avatar interaction streamed to the subject in each interactive session.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

Corresponding reference numerals are used to indicate corresponding parts throughout the several views.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Figure 1:
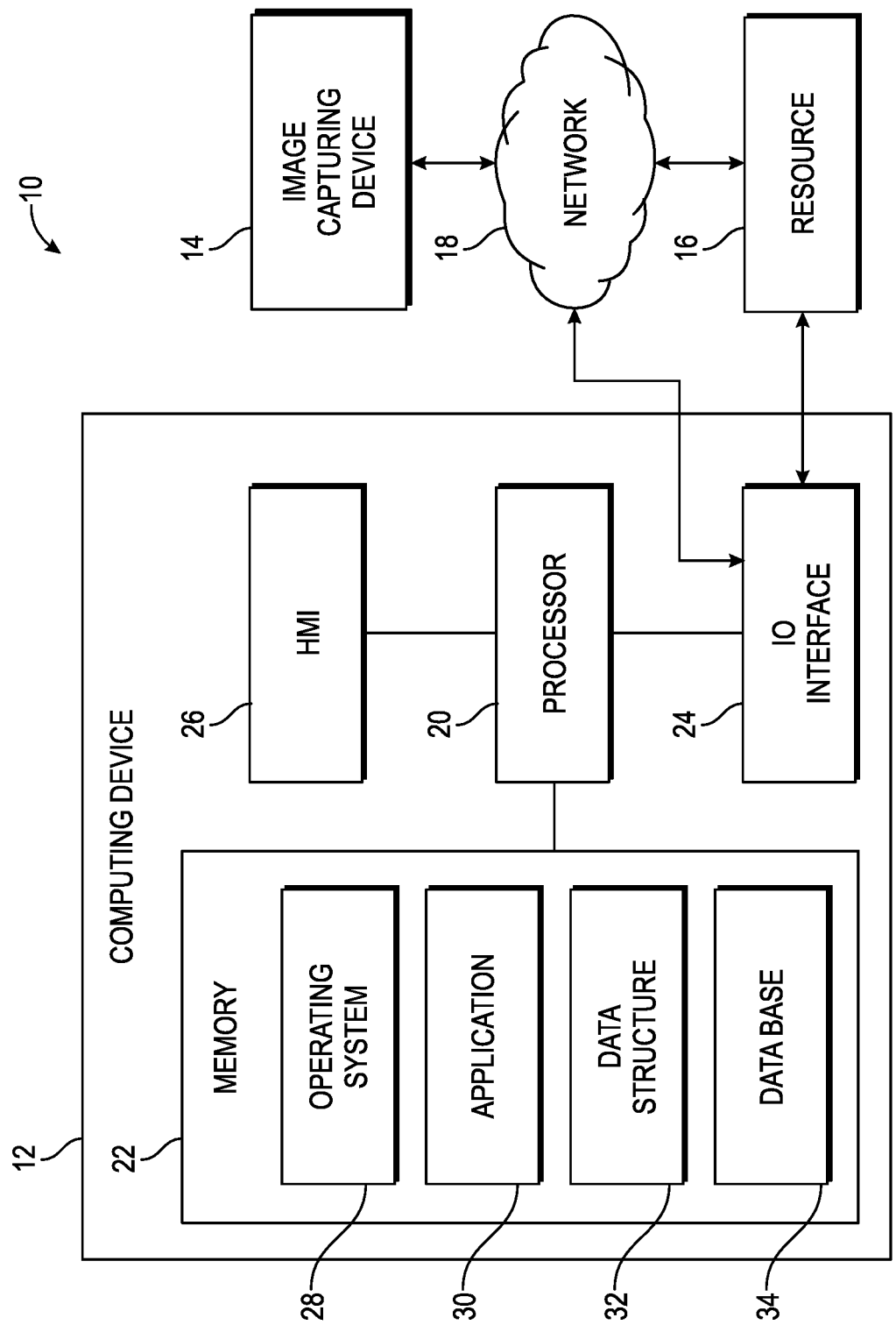
FIG. 1 illustrates a diagrammatic view of an exemplary virtual reality (VR) system including an avatar reaction computing device and an image capturing/streaming device that outputs avatars and surrounding environments comprised of images and/or audio signals to a subject to observe and change the behavior of the subject.

As shown in FIG. 1, the VR system 10 may include an avatar reaction computing device 12, an image capturing/streaming device 14, and an external resource 16. The avatar reaction computing device 12 may communicate with the image capturing/streaming device 14 and the external resource 16 through a network 18. The network 18 may include one or more private or public data networks, e.g., the Internet, that enable the exchange of data between systems connected to the network 18.

In some embodiments, the image capturing/streaming device 14 may be embodied as a wearable headset. In some embodiments, the image capturing/streaming device 14 includes an image streaming device configured to output a stream of images and an image capturing device configured to capture reaction data from a subject. In some embodiments, the image streaming device and the image capturing device may be physically separate from one another, and in other embodiments, both components may be included in the wearable headset. The image capturing device may be a camera, e.g., a video recording device, a brain scanning device, a thermal sensing device, or any other device known in the art and suitable for capturing reaction data from the subject.

The VR system 10 may also include an audio device configured to output audio signals. The avatar reaction computing device 12 may communicate with the audio device through the network 18. In some embodiments, the audio device may be included in the image capturing/streaming device 14, e.g., as a component of the wearable headset comprising the image capturing/streaming device 14, and in other embodiments, the audio device may be physically separate from one or both of the image streaming device and the image capturing device. It should be appreciated that one or more of the image streaming device, the audio device, and the image capturing device may be presented in any structural combination known in the art, as a single device or as two or more separate components.

The avatar reaction computing device 12 may include a processor 20, a memory 22, an input/output (I/O) interface 24, and a Human Machine Interface (HMI) 26. The avatar reaction computing device 12 may be operatively coupled to the external resource 16 via the network 18 or I/O interface 24. External resources may include, but are not limited to, servers, databases, mass storage devices, peripheral devices, cloud-based network services, cameras, sensors, or any other resource that may be used by the avatar reaction computing device 12 to implement embodiments of the invention.

The processor 20 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in memory 22. Memory 22 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, and/or data storage devices such as a hard drive, optical drive, tape drive, volatile or non-volatile solid state device, or any other device capable of storing data.

The processor 20 may operate under the control of an operating system 28 that resides in the memory 22. The operating system 28 may manage computer resources so that computer program code embodied as one or more computer software applications, such as an application 30 residing in the memory 22, may have instructions executed by the processor 20. The processor 20 may also execute the application 30 directly, in which case the operating system 28 may be omitted. The one or more computer software applications may include a running instance of an application comprising a server, which may accept requests from, and provide replies to, one or more corresponding client applications. One or more data structures 32 may also reside in the memory 22, and may be used by the processor 20, operating system 28, and/or application 30 to store or manipulate data.

The I/O interface 24 may provide a machine interface that operatively couples the processor 20 to other devices and systems, such as the external resource 16 or network 18. The application 30 may thereby work cooperatively with the external resource 16 or network 18 by communicating via the I/O interface 24 to provide the various features, functions, applications, processes, and/or modules comprising embodiments of the invention. The application 30 may also have program code that is executed by one or more external resources 16, or otherwise rely on functions or signals provided by other system or network components external to the avatar reaction computing device 12. Indeed, given the nearly endless hardware and software configurations possible, embodiments of the invention may include applications that are located externally to the avatar reaction computing device 12, distributed among multiple computers or other external resources 16, or provided by computing resources (hardware and software) that are provided as a service over the network 18, such as a cloud computing service.

The HMI 26 may be operatively coupled to the processor 20 of avatar reaction computing device 12 to enable a user to interact directly with the avatar reaction computing device 12. The HMI 26 may include video or alphanumeric streams, a touch screen, a handle-held remote, a speaker, and any other suitable audio and visual indicators capable of providing data to the user. The HMI 26 may also include input devices and controls such as an alphanumeric keyboard, a touch screen, a handle-held remote, a pointing device, keypads, pushbuttons, control knobs, microphones, etc., capable of accepting commands or input from the user and transmitting the entered input to the processor 20. The hand-held remote may use a Bluetooth chip to wirelessly output a constant stream of position, acceleration, and other data to the processor 20 of the avatar reaction computing device 12, or the held-held remote may output the data to the processor 20 in any other suitable way, and either in the form of a constant stream or non-continuous transmissions.

A database 34 may reside in the memory 22, and may be used to collect and organize data used by the various devices, systems, and modules described herein. The database 34 may include data and supporting data structures that store and organize the data. The database 34 may be arranged with any database organization or structure including, but not limited to, a relational database, a hierarchical database, a network database, an object-oriented database, or combinations thereof.

A database management system in the form of a computer software application executing as instructions on the processor 20 may be used to access data stored in records of the database 34 in response to a query, where the query may be dynamically determined and executed by the operating system 28, other applications 30, or one or more modules. Although embodiments of the invention may be described herein using relational, hierarchical, network, object-oriented, or other database terminology in specific instances, embodiments of the invention may use any suitable database management model, and are not limited to any particular type of database.

The image capturing/streaming device 14, and in some embodiments, in particular the image streaming device, may include one or more position sensors, which determine the orientation of the image/capturing streaming device 14. The image capturing/streaming device 14 may transmit the determined orientation of the image capturing/streaming device 14 to the processor 20 of the avatar reaction computing device 12 over the network 18.

As described, the image capturing/streaming device 14 may be embodied as a head-mounted device wearable by a subject. In use, the image device of the image capturing/streaming device 14 streams images to the subject utilizing the image capturing/streaming device 14. The images include of a plurality of interactive sessions. The interactive sessions each include at least an avatar and an environment in which each avatar is presented. Thus, a stream of images of one or more avatars and/or one or more environments in which each avatar is presented to a subject is referred to herein as an interaction, an avatar interaction, or an interactive session.

For each interactive session, at least one of an avatar and an environment in which the avatar is presented includes factors or characteristics associated therewith, which, when streamed to a subject, cause behavioral change of the subject. These factors or characteristics are described in greater detailed below.

Each avatar has a physical appearance based on that of the subject. For example, in a first interactive session, the image capturing/streaming device 14 streams a current-self avatar in a first virtual space. The current-self avatar is created from a plurality of images taken of the subject prior to the subject utilizing the image capturing/streaming device 14. The VR system 10 may further include a second image capturing device, e.g., a camera, operatively coupled to the network 18 and configured to capture images of the subject. The second image capturing device may transmit the images of the subject to the avatar reaction computing device 12 over the network 18.

The avatar reaction computing device 12 may create a 3D virtual representation of the subject, based on the transmitted images of the subject. The 3D virtual representation of the subject is referred to as an avatar. A first avatar has a physical appearance based on that of the subject at the present time, which may be referred to as the current-self avatar. Other avatars may represent the subject at a future time based on predicted changes to the physical appearance of the subject over time.

Certain characteristics or physical changes are associated with aging, e.g., gray hair, wrinkled skin, etc., and those characteristics may be stored in the memory 22 of the avatar reaction computing device 12. The characteristics or physical changes may be referred to as non-substance use characteristics. Certain other characteristics or physical changes are associated with continued substance use over time (i.e. alcohol or drug use), and such characteristics or physical changes may include a change in skin color, physical indicators of accelerated aging, undesired change in facial features, posture, body language, and clothing appearance. Those characteristics or physical changes may be stored in the memory 22 of the avatar reaction computing device 12.

In some embodiments, each avatar streamed to the subject includes a physical appearance that corresponds to a different physical appearance of the subject. For example, the avatar reaction computing device 12 may create a second avatar based on the images of the subject at the present time and based on the characteristics associated with substance use between the present time and a future time. The second avatar is referred to as a continued-use avatar. In the illustrative embodiment, the future time is 15 years from the present time; however, the future time may be any number of years—i.e. temporal delay—as selected by an operator of the avatar reaction computing device 12 or otherwise stored on the memory 22.

The avatar reaction computing device 12 may create a third avatar, which is referred to as a substance-free avatar. The substance-free avatar is created based on the images of the subject at the present time and based on the physical changes associated with aging of the subject to a future time without the occurrence of continued substance use. In the illustrative embodiment, the future time is 15 years from the present time; however, the future time may be any number of years as selected by an operator of the avatar reaction computing device 12 or otherwise stored on the memory 22.

The image capturing/streaming device 14 streams images of each avatar—i.e. current-self avatar, continued-use avatar, and substance-free avatar—to the subject in a predetermined order to cause and/or induce behavioral change of the subject. As used herein, behavioral change is the effect on the subject indicated by measured differences before and after treatment with the VR experience as illustrated and described herein. As used herein, induce or inducing behavioral change includes causation of immediate change or causation of delayed change in behavior as a result of the interactions presented to a subject. The term Future Reality Portal experience or VR experience is an experience output by the VR system 10 including the stream of each avatar and/or each environment in a predetermined order as described in more detail below. This disclosure contemplates treating a subject with any or all of the steps of the Future Reality Portal experience in one or more predetermined arrangements, which are stored in the memory 22, to cause behavioral change of the subject.

The image capturing/streaming device 14, e.g., the image capturing device, captures reaction data from the subject as the subject observes each interactive session streamed to the subject by the image capturing/streaming device 14. The reaction data is generated from the subject reacting to each avatar interaction streamed to the subject. The subject may react to each avatar interaction in the same or different ways, the different reactions resulting in different data being captured by the image capturing/streaming device 14. The reactions may be prompted as a result of the different physical appearances of each avatar or the different environments in which the avatars are presented, which represent a different corresponding outcomes of the subject based on decisions executed by the subject between the present time and the future time. In some embodiments, the avatar reaction computing device 12 receives the captured reaction data from the image capturing/streaming device 14 through the network 18. In some embodiments, avatar reaction computing device 12 incorporates the reaction data into a psychological assessment of the subject based on how the subject reacted to each avatar interaction streamed to the subject in each interactive session. In other embodiments, the reaction data is processed manually, and likewise, in other embodiments, the psychological assessment of the subject is constructed manually.

Prior to the Future Reality Portal experience, the subject may be interviewed regarding relevant personal details, some general, and some specific to the condition to be modified, e.g., substance abuse. The personal details provided by the subject may be referenced by one or more avatars, i.e. with audio signals output by the audio device, as will be described herein. The realism of the Future Reality Portal experience is further magnified by multi-sensory engagement such as haptic and olfactory engagement. For example, physical objects nearby the subject are spatially aligned with images streamed to the subject by the image capturing/streaming device 14. The physical object may be spatially aligned with images streamed by the image capturing/streaming device 14 through a calibration process. For example, the calibration process may include steps performed by an operator prior to the subject's Future Reality Portal experience.

For example, during the calibration process, the operator may move the HMI 26 or another HMI, e.g., a hand-held remote, along the physical object. The hand-held remote may send signals to the processor 20 indicative of the location, shape, and size of the physical object. Based on the signals received from the hand-held remote, the avatar reaction computing device 12 may determine the relative position in a virtual space of an image representing the physical object. In response to signals received from the avatar reaction computing device 12, the image capturing/streaming device 14 streams images to the subject of the physical object in the virtual space. The images are streamed to the subject only in response to the image capturing/streaming device 14 being positioned in an orientation or direction in which the physical object is actually present in reality. This haptic engagement increases the realism of the Future Reality Portal experience to the subject.

In addition to haptic engagement, the Future Reality Portal experience also includes olfactory engagement in which an odorant is administered representing a scent likely to be present in the scene streamed to the subject in the virtual space. For example, in an embodiment in which the subject is sitting on a bench in a grassy park, a grass-scent may be administered. A scent-releasing device may house an odorant, which could be released in a context-dependent manner. Further, in some embodiments, the releasing device may be coupled to the bench. In some embodiments, the scent-releasing device may include a lid coupled to an opening mechanism of the device. The opening mechanism may be coupled to a manually operable switch or may be coupled to the avatar reaction computing device 12. In some embodiments, the avatar reaction computing device 12, may activate the opening mechanism to open the lid of the scent-releasing device, and/or engage an electric fan, when the image capturing/streaming device 14 streams a certain virtual reality space to the subject, i.e. the second virtual reality space, i.e. the grassy park.

In some embodiments, each virtual reality space is associated with a different scent-releasing device. In some embodiments, each avatar is associated with a different scent-releasing device.

Figure 2:
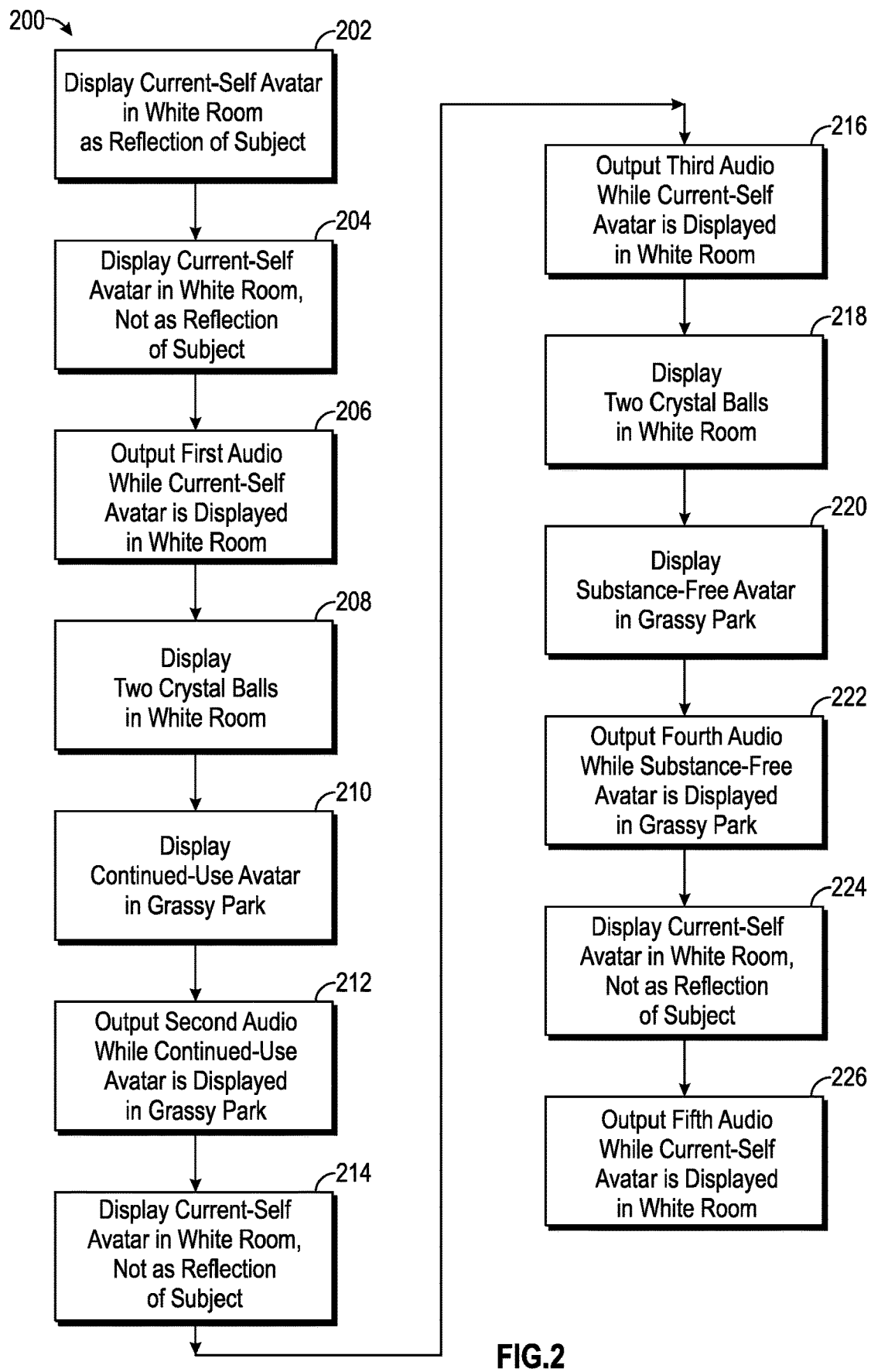
FIG. 2 illustrates a flow chart showing algorithmic steps performed by the VR system, which are related to streaming avatars that are stored in a memory of the avatar reaction computing device.
Figure 3:
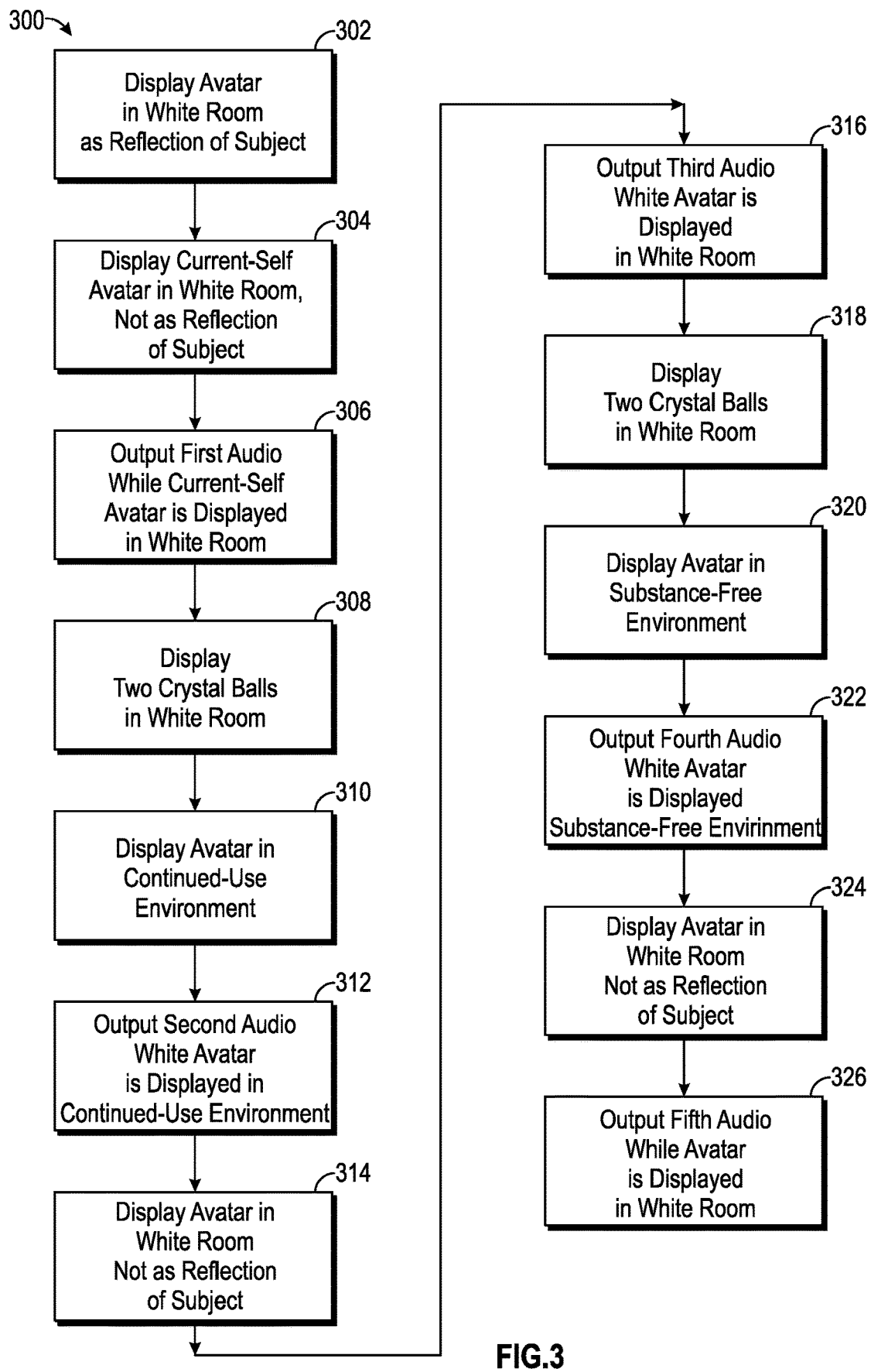
FIG. 3 illustrates a flow chart showing algorithmic steps, which are performed by the VR system and related to streaming environments in which the avatars are presented, wherein the environments are stored in a memory of the avatar reaction computing device.
Figure 4:
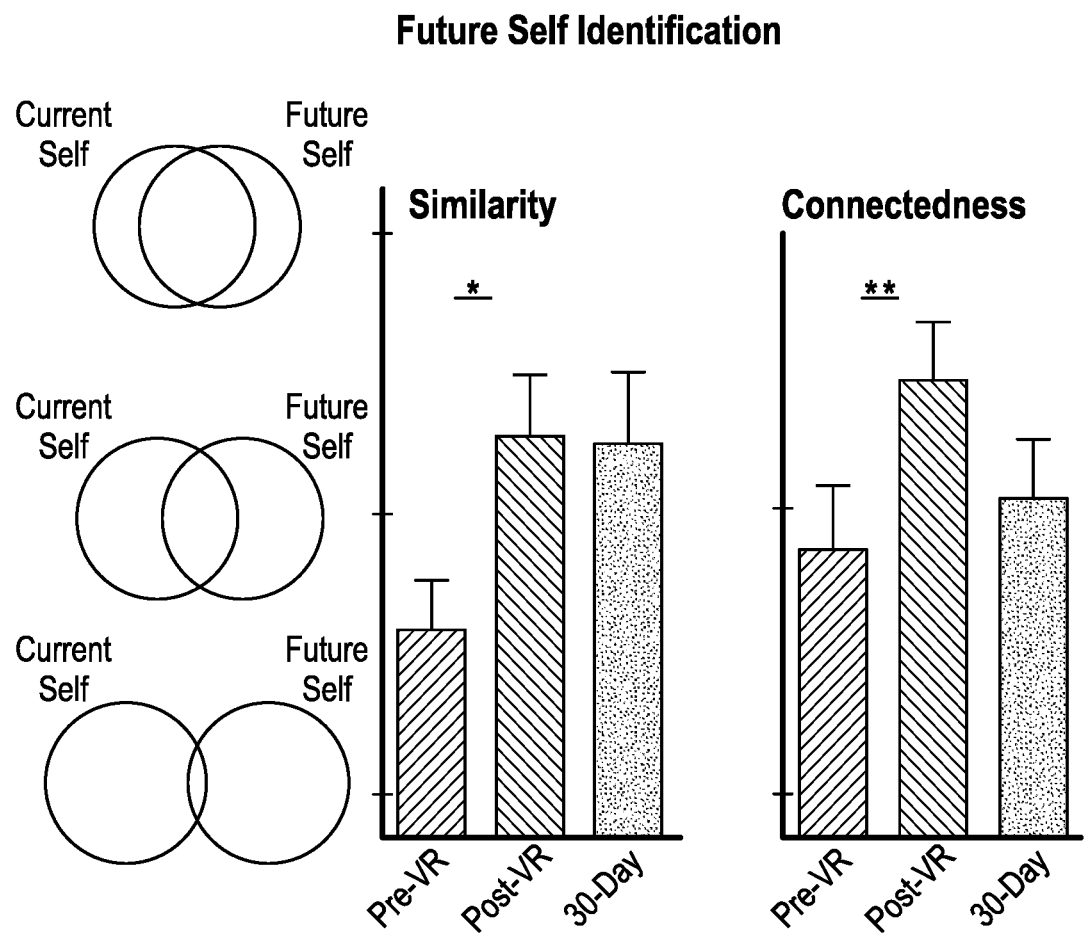
FIG. 4 illustrates the effects of the VR experience on future self-identification, pre- and post-VR, and 30 days later in subjects in early recovery (n=18) from a substance use disorder for future self-similarity (left) and future self-connectedness (right); means±standard error of mean significance indicated as $**p<0.01$, $*p<0.05$. These data show that the VR experience increases self-reported identification with a future version of the self.
Figure 5:
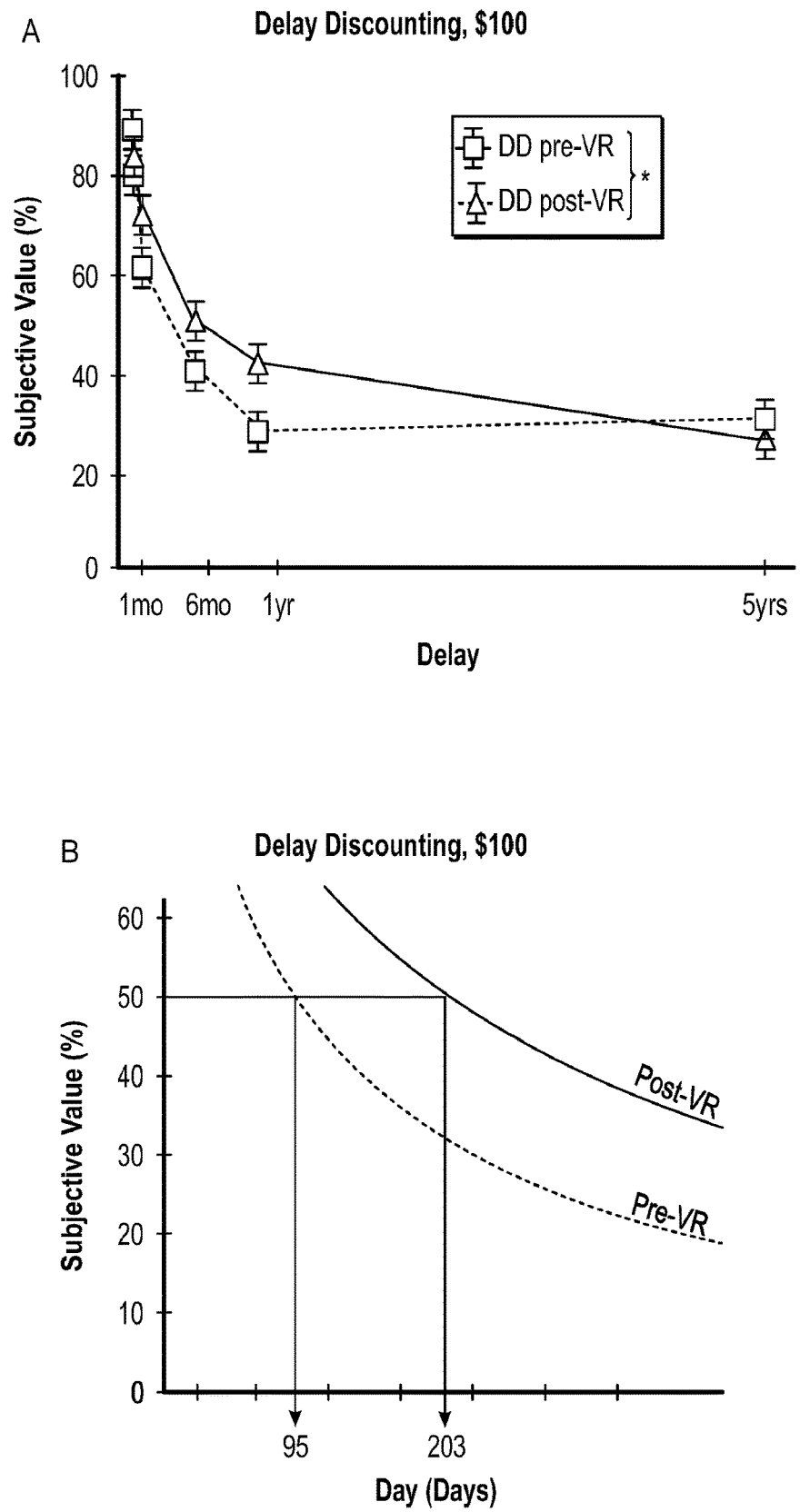
FIG. 5 illustrates the effect of the VR experience on delay discounting—the relative preference for immediate versus delayed monetary rewards—such that (A) post-VR, preference for delayed rewards is increased, and (B) after nonlinear regression (to quantify delay tolerance), showed a doubling of the amount of delay a subject was willing to wait to receive the reward. These data show that the VR experience changes choice behavior, i.e., increases preference for delayed rewards, $*p<0.05$.
Figure 6:
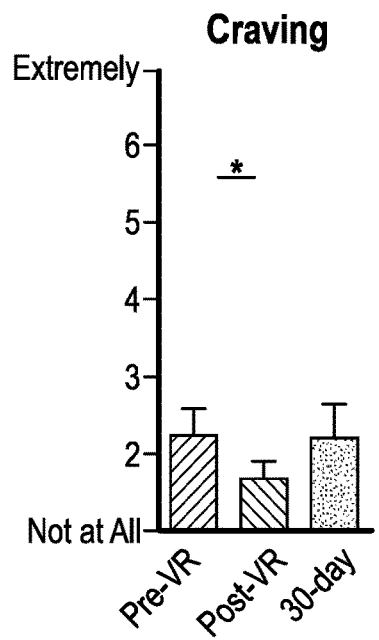
FIG. 6 illustrates VR-induced reduction in drug craving on the day of the VR experience, $*p<0.05$.
Figure 7:
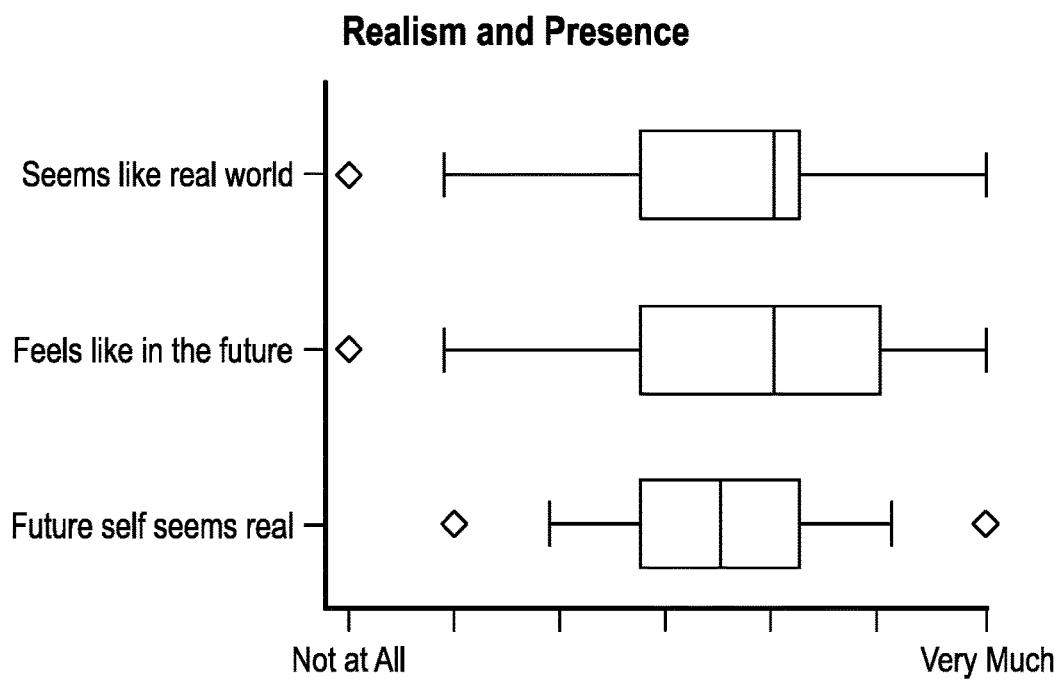
FIG. 7. illustrates ratings of realism and 'presence' from three different self-report items, indicating that the experience was plausibly realistic.
Figure 8:
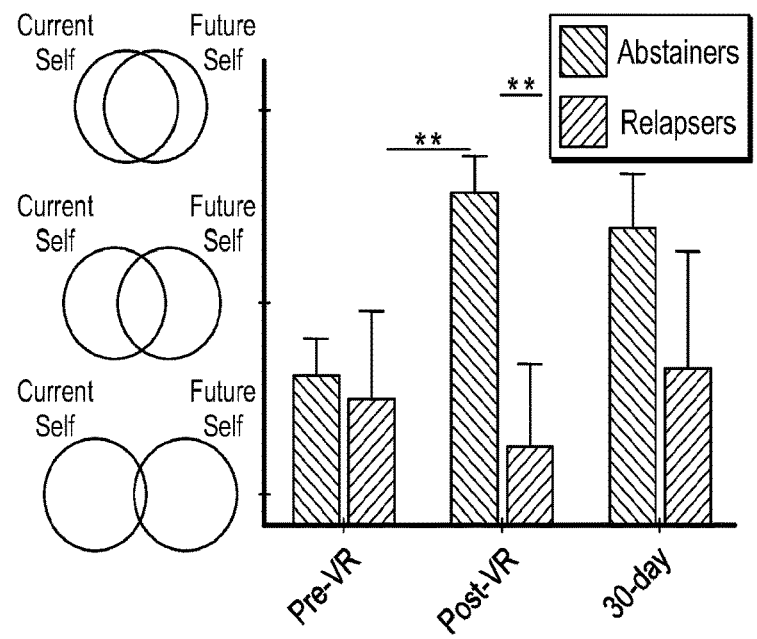
FIG. 8 illustrates (A) how subjects who remained drug abstinent 30 days later (n=15) showed a significant positive response to the VR experience, while subjects who relapsed (n=3) did not show such a response; (B) individual ratings shown for abstainers (solid lines) and relapsers (dotted lines); $*p<0.05$, $**p<0.01$.
Figure 8:
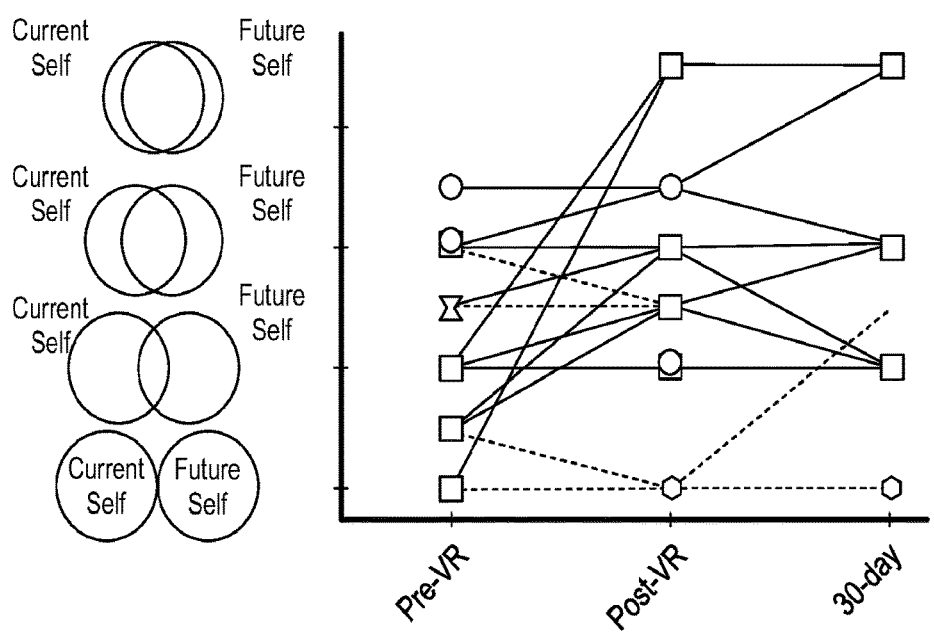

Referring now to FIG. 2, the method 200 illustrates steps performed by the VR system 10. As suggested by step 202, in use, the image capturing/streaming device 14 initially streams a first interactive session including a first virtual reality space, which may be referred to as the white room. In response to the image capturing/streaming device 14 being positioned in a predetermined orientation, the image capturing/streaming device 14 streams a mirror in the white room. While the image capturing/streaming device 14 remains within a predetermined threshold of the predetermined orientation, the image capturing/streaming device 14 streams a first series of images of the first avatar as a real-time reflection of the subject. In other words, the subject sees the current-self avatar as the subject's reflection in a mirror. The subject may nod up and down and side to side, with precise avatar mimicry, reinforcing avatar connectedness through a phenomenon known as body transfer. It should be appreciated that, in some embodiments, the image capturing/streaming device 14 need not be positioned in a predetermined orientation to advance the process.

As shown in FIG. 2, during the first interactive session, after streaming the current-self avatar in the white room as a reflection of the subject, at step 204, the image capturing/streaming device 14 streams the current-self avatar once again in the white room, although this time, the current-self avatar is not streamed as a reflection of the subject. At this step in the process, the image capturing/streaming device 14 is also streaming the physical object in the virtual space, i.e. a first bench, as well as a second bench, which does not exist in the physical world. The current-self avatar is streamed as sitting on the second bench. As suggested in FIG. 2, at step 206, the audio device 15 outputs a first audio signal while the current-self avatar is streamed as sitting on the second bench. The first audio signal may comprise a plurality of messages that are output audibly to the subject. For example, a first message may invite the subject to sit on the first bench. A second message may invoke personal identifiers based on the personal details provided by the subject and stored in the memory 22 prior to the Future Reality Portal experience. A third message may urge the subject to "choose a future" and "time travel," e.g., 15 years, into the future.

As suggested by FIG. 2, at step 208, during the first interactive streaming session, the image capturing/streaming device 14 streams two new images, which represent options to the subject, e.g., two large crystal balls. The audio device 15 outputs the third message while the crystal balls are being streamed. It should be appreciated that crystal balls as used herein are exemplary representations of options selectable by the subject and may be embodied as numerous other images sufficient to represent options available to the subject.

At step 210, the image capturing/streaming device 14 streams a second interactive session including the continued-use avatar the in second virtual space, e.g., a grassy park. Step 210 may occur, in response to the image capturing/streaming device 14 being positioned in a predetermined orientation (i.e. when the subject looks at one of the crystal balls). In the second interactive session, the continued-use avatar is streamed as sitting on the second bench in the grassy park. The continued-use avatar may be slouched, unkempt, and distressed-looking. It should be appreciated that, in some embodiments, the image capturing/streaming device 14 need not be positioned in a predetermined orientation to advance the process.

As suggested by FIG. 2, at step 212, in the second interactive session, the audio device outputs a second audio signal while the continued-use avatar is streamed as sitting on the second bench in the grassy park. The second audio signal may include a message stating, e.g., that "life's important things" were lost to substance use, that the year in which the subject experienced the Future Reality Portal was a missed opportunity for recovery, and "don't let this happen to us." This message is based on the personal details provided by the subject and stored in the memory 22 prior to the Future Reality Portal experience.

As suggested by FIG. 2, the after the audio device outputs the second audio signal, at step 214, the image capturing/streaming device 14 streams an additional interactive session including the current-self avatar in the white room on the second bench. At step 214, the current-self avatar is not streamed as a reflection of the subject, i.e., the current-self is independently animated. As suggested by FIG. 2, at step 216, in the additional interactive session, the audio device outputs a third audio signal while the current-self avatar is streamed as sitting on the second bench. Simultaneously, at step 218, the crystal balls, e.g., are streamed by the image capturing/streaming device 14. The third audio signal may include a message urging the subject to select the other future—i.e. the other option.

At step 220, the image capturing/streaming device 14 streams a third interactive session including the substance-free avatar in the second virtual space, i.e., the grassy park. In some embodiments, step 220 occurs in response to the image capturing/streaming device 14 being positioned in a predetermined orientation (i.e. when the subject looks at the second of the two crystal balls). The substance-free avatar is streamed as sitting on the second bench in the grassy park. The substance-free avatar may appear neater, healthier, cleaner, and more positive than the continued-use avatar appeared. It should be appreciated that, in some embodiments, the image capturing/streaming device 14 need not be positioned in a predetermined orientation to advance the process.

As suggested by FIG. 2, at step 222, in the third interactive session, the audio device outputs a fourth audio signal while the substance-free avatar is streamed as sitting on the second bench in the grassy park. The third audio signal may include a message stating, e.g., that a substance-free journey allowed for the realization of dreams and goals. This message is based on the personal details provided by the subject and stored in the memory 22 prior to the Future Reality Portal experience.

As suggested by FIG. 2, the after the audio device outputs the fourth audio signal, at step 224, the image capturing/streaming device 14 streams a fourth interactive session including the current-self avatar once again in the white room on the second bench. At step 224, the current-self avatar is not streamed as a reflection of the subject. As suggested by FIG. 2, at step 226, in the fourth interactive session, the audio device outputs a fifth audio signal while the current-self avatar is streamed as sitting on the second bench. The fifth audio signal may include a message, e.g., encouraging the subject and reinforcing continuity between present action and future outcomes.

In some embodiments, for each interactive session, the physical appearance of each avatar may be the same; however, the environment in which each avatar is presented may be different. In some embodiments, the environments streamed to the subject may include differences in material items desired by the subject. In some embodiments, the environments streamed to the subject may include differences in indicators of affluence as perceived by the subject. Certain factors or characteristics are associated with affluence, e.g., the cleanliness, newness, and type material used to construct surrounding objects. Such indicators of affluence may be stored in the memory 22 of the avatar reaction computing device 12. Further, during the interview regarding relevant personal details of the subject, the subject may indicate certain desired material items, e.g., a boat or a new car. Such material items may be stored in the memory 22 of the avatar reaction computing device 12. Positive versions (or in some instances, mere presence) of the indicators of affluence and the desired material items may be referred to as non-substance use characteristics of the environment in which each avatar is presented. Negative versions (or in some instances, utter lack) of indicators of affluence and the desired material items may be referred to as substance use characteristics of the environment in which each avatar is presented.

The subject's current environment may be described as an environment that includes the indicators of affluence and the desired material items that the subject currently possesses. A continued-use environment and a substance-free environment each represent different corresponding outcomes of the subject based on decisions executed by the subject between the present time and the future time. For example, the continued-use environment represents the indicators of affluence and the desired material items associated with the subject with continued substance use from the present time to a future time, and the substance-free environment represents the indicators of affluence and the desired material items associated with the subject with no substance use from the present time to a future time.

Thus, in some embodiments, the image capturing/streaming device 14 streams images of each environment—i.e. a current environment, a continued-use environment, and a substance-free environment—to the subject in a predetermined order to cause and/or induce behavioral change of the subject. This disclosure contemplates treating a subject with any or all of the steps shown in method 300 of the Future Reality Portal experience in one or more predetermined arrangements to cause behavioral change of the subject. Such steps are stored in the memory 22. The steps of the method 300 are generally the same as the steps of the method 200 except that the different physical appearances of the avatars are replaced with different environments in which the avatars are presented.

In some embodiments, for each interactive session, the capturing/streaming device 14 may stream different physical appearances of avatars and different environments in which each avatar is presented simultaneously. Thus, any number of different characteristics of avatars and/or of environments each associated with substance or alcohol use or non-use may be streamed to the subject to cause behavioral change of the subject when observed by the subject in a Future Reality Portal experience.

While the image streaming device is streaming each interactive session, the image capturing device, is capturing reaction data from the subject as the subject observes each interactive session. In some embodiments, the avatar reaction computing device 12 receives the captured reaction data from the image capturing/streaming device 14 through the network 18. In some embodiments, avatar reaction computing device 12 incorporates the reaction data into a psychological assessment of the subject based on how the subject reacted to each avatar interaction streamed to the subject in each interactive session.

The Future Reality Portal experience has been shown in studies to be successful in addressing a critical need for increasing future orientation (as measured by behavior change) by interacting with representations of one's future-self to establish continuity between present action and future outcomes. Relapse rates for alcohol and substance use disorders remain high and leads to serious consequences and costs. Substance use disorder is largely characterized by impairment of delaying gratification. An immersive virtual reality intervention, presented in the manner described herein, increases (i.e., directs attention toward) the future orientation in early recovery participants, which are also referred to herein as subjects. This intervention aims to increase valuation of non-drug/alcohol future rewards by presenting personalized healthy rewards and outcomes. The effects of the VR intervention on delay-of-reward with the delay discounting task (DD) has been assessed and is described herein. The effect of future and present cues on brain activation during delay discounting has also been determined with functional magnetic resonance imaging (fMRI).

In a pilot study represented by FIGS. 4-8, subjects' brain responses to visual portrayals of the VR experience were tested, both during an introspective state and during task. The introspective state was measured while subjects viewed a video of the future self on the virtual park bench, without any interaction, compared to a control condition of just the park bench with no avatar. While viewing the future self, functional connectivity was increased between the posterior cingulate cortex and the dorsolateral prefrontal cortex. During fMRI that presented a task, where subjects performed delay discounting in the MRI scanner while seeing images of their future self and present self avatars, the future self increased activation of the posterior cingulate cortex and precuneus (fMRI data results significant at p<0.005, cluster size=40 voxels). Together, these results demonstrate that the VR experience increases introspective-executive network brain activation at 'rest', and increases introspective-prospective region activation during intertemporal decision-making.

These findings demonstrate paradigm feasibility and behavioral efficacy of using immersive virtual reality to enhance future orientation (e.g., valuation and focus on future outcomes) in recovering participants. The study implicates precuneus activation in episodic and future-self mental imagery. Together, these preliminary data suggest a critical role of the posterior cingulate cortex and precuneus in modulating choice when considering future rewards.

While the disclosure has been illustrated and described in detail in the drawings and foregoing description, such illustration and description is to be considered as exemplary and not restrictive in character, it being understood that illustrative embodiment(s) have been shown and described and that all changes and modifications that come within the spirit of the disclosure are initial to be protected. It will be noted that alternative embodiments of the present disclosure may not include all of the features described yet still benefit from at least some of the advantages of such features. Those of ordinary skill in the art may readily devise their own implementations that incorporate one or more of the features of the present disclosure and fall within the spirit and scope of the present invention as defined by the appended claims.

What is claimed is:

1. A behavioral change observation system for inducing a behavioral change of a subject generated via a plurality of virtual reality interactions with a plurality of avatars, the system comprising:

an image capturing/streaming device configured to capture a reaction of the subject as the subject is responding to each interactive session that is streamed to the subject;

one or more processors in communication with the image capturing/streaming device; and a memory in communication with the one or more processors and storing program code that, when executed by at least one of the one or more processors, causes the system to: stream to the subject utilizing the image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment that each avatar is presented in corresponds to an outcome of the subject based on decisions executed by the subject between a present time and a future time;

wherein each avatar streamed to the subject includes a physical appearance that corresponds to a different physical appearance of the subject;

wherein the one or more processors is further configured to cause the system to: stream a first interactive session that includes a first avatar interaction with a first avatar having a physical appearance based on a current physical appearance of the subject; and stream at least one additional interactive session that includes at least one additional avatar interaction with at least one additional avatar that has an aged physical appearance that is associated with aging of the subject to the future time;

wherein the at least one additional interactive session includes: a second interactive session that includes a second avatar interaction with a second avatar that has an aged substance use physical appearance based on characteristics associated with substance use by the subject between the present time and the future time; and a third interactive session that includes a third avatar interaction with a third avatar that has an aged non-substance use physical appearance based on characteristics associated with a substance free existence of the subject between the present time and the future time;

wherein the at least one processor is further configured to: stream the first interactive session including the first avatar in a first virtual space, followed by the stream of the second interactive session including the second avatar in a second virtual space, followed by the stream of the third interactive session including the third avatar in the second virtual space; and wherein the at least one processor is further configured to: stream a first series of images of the first avatar in the first virtual space as a real-time reflection of the subject during the first interactive session of the first avatar interaction; and stream, subsequently, a second series of images of the first avatar in the first virtual space whereby the first avatar is not streamed as a reflection of the subject during the second interactive session.

2. The system of claim 1, wherein the one or more processors is further configured to cause the system to:

capture reaction data from the subject as the subject observes each interactive session streamed to the subject, wherein the reaction data is generated from the subject reacting to each avatar interaction streamed to the subject, and incorporate the reaction data into a psychological assessment of the subject based on how the subject reacted to each avatar interaction streamed to the subject in each interactive session.

3. The system of claim 1, wherein each environment in which each avatar is presented in includes differences in at least one of: (i) material items desired by the subject and (ii) general indicators of affluence.

4. The system of claim 1, wherein the at least one processor is further configured to:

identify that the image capturing/streaming device is positioned in a first orientation; and stream the second series of images of the first avatar in response to identifying that the image capturing/streaming device is positioned in the first orientation during the first interactive session.

5. A behavioral change observation system for inducing a behavioral change of a subject generated via a plurality of virtual reality interactions with a plurality of avatars, the system comprising:

an image capturing/streaming device configured to capture a reaction of the subject as the subject is responding to each interactive session that is streamed to the subject;

one or more processors in communication with the image capturing/streaming device; and a memory in communication with the one or more processors and storing program code that, when executed by at least one of the one or more processors, causes the system to: stream to the subject utilizing the image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment that each avatar is presented in corresponds to an outcome of the subject based on decisions executed by the subject between a present time and a future time;

wherein each avatar streamed to the subject includes a physical appearance that corresponds to a different physical appearance of the subject;

wherein the one or more processors is further configured to cause the system to: stream a first interactive session that includes a first avatar interaction with a first avatar having a physical appearance based on a current physical appearance of the subject; and stream at least one additional interactive session that includes at least one additional avatar interaction with at least one additional avatar that has an aged physical appearance that is associated with aging of the subject to the future time;

wherein the at least one additional interactive session includes: a second interactive session that includes a second avatar interaction with a second avatar that has an aged substance use physical appearance based on characteristics associated with substance use by the subject between the present time and the future time; and a third interactive session that includes a third avatar interaction with a third avatar that has an aged non-substance use physical appearance based on characteristics associated with a substance free existence of the subject between the present time and the future time;

wherein the at least one processor is further configured to: stream the first interactive session including the first avatar in a first virtual space, followed by the stream of the second interactive session including the second avatar in a second virtual space, followed by the stream of the third interactive session including the third avatar in the second virtual space; and wherein the at least one processor is further configured to: output a first audio signal from an audio device included in the image capturing/streaming device when the image of the first avatar is streamed in the first virtual space;

output a second audio signal from the audio device when the image of the second avatar is streamed in the second virtual space; and output a third audio signal from the audio device when the image of the third avatar is streamed in the second virtual space.

6. The system of claim 5, wherein the at least one processor is further configured to:

stream additional images including the first avatar in the first virtual space during a fourth interactive session subsequent to streaming images including the third avatar in the second virtual space during the third interactive session; and output a fourth audio signal from the audio device when the image of the first avatar is streamed during the fourth interactive session.

7. A behavioral change observation system for inducing a behavioral change of a subject generated via a plurality of virtual reality interactions with a plurality of avatars, the system comprising:

an image capturing/streaming device configured to capture a reaction of the subject as the subject is responding to each interactive session that is streamed to the subject;

one or more processors in communication with the image capturing/streaming device; and a memory in communication with the one or more processors and storing program code that, when executed by at least one of the one or more processors, causes the system to: stream to the subject utilizing the image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment that each avatar is presented in corresponds to an outcome of the subject based on decisions executed by the subject between a present time and a future time;

wherein each avatar streamed to the subject includes a physical appearance that corresponds to a different physical appearance of the subject;

wherein the one or more processors is further configured to cause the system to: stream a first interactive session that includes a first avatar interaction with a first avatar having a physical appearance based on a current physical appearance of the subject; and stream at least one additional interactive session that includes at least one additional avatar interaction with at least one additional avatar that has an aged physical appearance that is associated with aging of the subject to the future time;

wherein the at least one additional interactive session includes: a second interactive session that includes a second avatar interaction with a second avatar that has an aged substance use physical appearance based on characteristics associated with substance use by the subject between the present time and the future time; and a third interactive session that includes a third avatar interaction with a third avatar that has an aged non-substance use physical appearance based on characteristics associated with a substance free existence of the subject between the present time and the future time;

wherein the at least one processor is further configured to: stream the first interactive session including the first avatar in a first virtual space, followed by the stream of the second interactive session including the second avatar in a second virtual space, followed by the stream of the third interactive session including the third avatar in the second virtual space; and wherein the at least one processor is further configured to: identify that the image capturing/streaming device is positioned in a second orientation during the first interactive session;

identify that the image capturing/streaming device is positioned in a third orientation during an additional interactive session;

stream images including the second avatar in the second virtual space during the second interactive session in response to identifying that the image capturing/streaming device is positioned in the second orientation during the first interactive session; and stream images including the third avatar in the second virtual space during the third interactive session in response to identifying that the image capturing/streaming device is positioned in the third orientation during the additional interactive session.

8. A method for inducing a behavioral change of a subject generated via a plurality of virtual reality interactions with a plurality of avatars, the method comprising: streaming to the subject utilizing an image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment in which each avatar is presented in corresponds to different outcomes of the subject based on decisions executed by the subject between a present time and a future time, wherein the environment in which each avatar is presented is based on at least one of material items desired by the subject and general indicators of affluence;

wherein streaming images to a subject utilizing an image capturing/streaming device further includes: streaming a first interactive session that includes a first avatar interaction with a first avatar having a physical appearance based on a current physical appearance of the subject; and streaming at least one additional interactive session that includes at least one additional avatar interaction with at least one additional avatar that has an aged physical appearance that is associated with aging of the subject to the future time;

wherein streaming at least one additional interactive session that includes at least one additional avatar interaction with at least one additional avatar includes: streaming a second interactive session that includes a second avatar interaction with a second avatar that has an aged substance use physical appearance based on characteristics associated with substance use by the subject between the present time and the future time; and streaming a third interactive session that includes a third avatar interaction with a third avatar that has an aged non-substance use physical appearance based on characteristics associated with a substance free existence of the subject between the present time and the future time;

wherein streaming images to a subject utilizing an image capturing/streaming device further includes: streaming the first interactive session including the first avatar in a first virtual space, followed by streaming the second interactive session including the second avatar in a second virtual space, followed by streaming the third interactive session including the third avatar in the second virtual space; and wherein streaming images to a subject utilizing an image capturing/streaming device further includes: streaming a first series of images of the first avatar in the first virtual space as a real-time reflection of the subject during the first interactive session of the first avatar interaction; and streaming, subsequently, a second series of images of the first avatar in the first virtual space whereby the first avatar is not streamed as a reflection of the subject during the second interactive session.

9. The method of claim 8, wherein streaming images to a subject utilizing an image capturing/streaming device further includes:
   capturing reaction data from the subject as the subject observes each interactive session streamed to the subject, wherein the reaction data is generated from the subject reacting to each avatar interaction streamed to the subject including each avatar and each corresponding physical appearance of each avatar, and
   incorporating the reaction data into a psychological assessment of the subject based on how the subject reacted to each avatar interaction streamed to the subject in each interactive session.

10. The method of claim 8, further comprising:
    identifying that the image capturing/streaming device is positioned in a first orientation; and
    wherein streaming images to a subject utilizing an image capturing/streaming device further includes:
    streaming the second series of images of the first avatar in response to identifying that the image capturing/streaming device is positioned in the first orientation.

11. A method for inducing a behavioral change of a subject generated via a plurality of virtual reality interactions with a plurality of avatars, the method comprising:
    streaming to the subject utilizing an image capturing/streaming device a plurality of interactive sessions with each interactive session that is streamed including an interaction with an avatar from a plurality of interactions with avatars and an environment in which each avatar is presented in from a plurality of environments in which each avatar is presented in, wherein at least one of: (i) a physical appearance of each avatar and (ii) the environment in which each avatar is presented in corresponds to different outcomes of the subject based on decisions executed by the subject between a present time and a future time, wherein the environment in which each avatar is presented is based on at least one of material items desired by the subject and general indicators of affluence;
    wherein streaming images to a subject utilizing an image capturing/streaming device further includes: streaming a first interactive session that includes a first avatar interaction with a first avatar having a physical appearance based on a current physical appearance of the subject; and streaming at least one additional interactive session that includes at least one additional avatar interaction with at least one additional avatar that has an aged physical appearance that is associated with aging of the subject to the future time;
    wherein streaming at least one additional interactive session that includes at least one additional avatar interaction with at least one additional avatar includes: streaming a second interactive session that includes a second avatar interaction with a second avatar that has an aged substance use physical appearance based on characteristics associated with substance use by the subject between the present time and the future time; and streaming a third interactive session that includes a third avatar interaction with a third avatar that has an aged non-substance use physical appearance based on characteristics associated with a substance free existence of the subject between the present time and the future time;
    wherein streaming images to a subject utilizing an image capturing/streaming device further includes: streaming the first interactive session including the first avatar in a first virtual space, followed by streaming the second interactive session including the second avatar in a second virtual space, followed by streaming the third interactive session including the third avatar in the second virtual space; and
    wherein the method further comprises: identifying that the image capturing/streaming device is positioned in a second orientation during the first interactive session; and identifying that the image capturing/streaming device is positioned in a third orientation during an additional interactive session;
    wherein streaming images including the second avatar in the second virtual space includes doing so in response to identifying that the image capturing/streaming device is positioned in the second orientation during the first interactive session; and
    wherein streaming images including the third avatar in the second virtual space includes doing so in response to identifying that the image capturing/streaming device is positioned in the third orientation during the additional interactive session.

* * * * *